United States Patent [19]

Franz

[11] 3,950,402
[45] Apr. 13, 1976

[54] PROCESS FOR PRODUCING N-PHOSPHONOMETHYL GLYCINE

[75] Inventor: John E. Franz, Crestwood, Mo.

[73] Assignee: Monsanto Company, St. Louis, Mo.

[22] Filed: Feb. 16, 1973

[21] Appl. No.: 333,414

Related U.S. Application Data

[63] Continuation-in-part of Ser. No. 258,281, May 31, 1972.

[52] U.S. Cl. .............................................. 260/502.5
[51] Int. Cl.² .......................................... C07F 9/38
[58] Field of Search ................................. 260/502.5

[56] References Cited
UNITED STATES PATENTS

| | | | |
|---|---|---|---|
| 3,288,846 | 11/1966 | Irani et al. | 260/502.5 |
| 3,429,914 | 2/1969 | Crutchfield et al. | 260/502.5 |
| 3,796,749 | 3/1974 | Krueger et al. | 260/502.5 |

OTHER PUBLICATIONS

Van Wazer, "Phosphorus and its Compounds", Vol. 1, (1958), p. 379.

*Primary Examiner*—Joseph E. Evans
*Attorney, Agent, or Firm*—William T. Black; Donald W. Peterson

[57] ABSTRACT

N-phosphonomethyl glycine is produced by the oxidation of N-(phosphonomethyl) iminodiacetic acid. N-(Phosphonomethyl) iminodiacetic acid is heated to an elevated temperature in an aqueous medium and an oxidizing agent ($H_2O_2$, air plus a catalyst such as platinum, palladium, rhodium, etc.) added to oxidize the N-(phosphonomethyl) iminodiacetic acid to N-phosphonomethyl glycine, which is recovered by crystallization.

13 Claims, No Drawings

PROCESS FOR PRODUCING N-PHOSPHONOMETHYL GLYCINE

This application is a continuation-in-part of my co-pending application Serial Number 258,281, filed May 31, 1972.

This invention relates to a method of producing N-phosphonomethyl glycine by the oxidation of N-(phosphonomethyl) iminodiacetic acid. More particularly, this invention relates to the production of N-phosphonomethyl glycine by the oxidation of N-(phosphonomethyl) iminodiacetic acid with an oxidizing agent such as hydrogen peroxide or a free oxygen-containing gas with a metal catalyst.

In accordance with the process of this invention, N-(phosphonomethyl) iminodiacetic acid having the formula

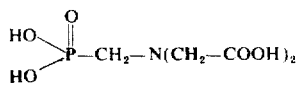

is mixed with water and heated to an elevated temperature. The oxidizing agent is then added and the iminodiacetic acid oxidatively converted into N-phosphonomethyl glycine and other decomposition products. The N-phosphonomethyl glycine is then isolated by precipitation, for example, by the addition of a water-miscible organic solvent, evaporation of water, or cooling.

The manner of reacting the N-(phosphonomethyl) iminodiacetic acid with the oxidizing agent is not critical and can be accomplished in many ways. For example, one can form an admixture of reactants and then heat the mixture to the temperature of reaction in a suitable vessel to convert the N-(phosphonomethyl) iminodiacetic acid to N-phosphonomethyl glycine. Alternatively, the oxidizing agent can be added to a mixture of N-(phosphonomethyl) iminodiacetic acid and water which mixture has been preheated to the reaction temperature and the mixture continued to be heated at the elevated temperature to cause the oxidation and conversion of the N-(phosphonomethyl) iminodiacetic acid into N-phosphonomethyl glycine.

It is believed that the reaction takes place in accordance with the following equation which, for simplicity, shows hydrogen peroxide as the oxidizing agent:

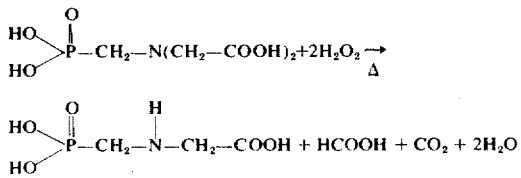

In conducting the process of this invention, the temperature of reaction can be from as low as 20°C. to 125°C. or even higher. It is preferred, for ease of reaction and to obtain the best yield of product, to conduct the process of this invention from about 70°C. to about 120°C.

The ratio of reactants, that is, the oxidizing agent and the N-(phosphonomethyl) iminodiacetic acid, is not narrowly critical. As is apparent from the above equation, for best yields and ease of recovery of the reaction product, that is the N-phosphonomethyl glycine, one should employ at least 2 moles of the oxidizing agent ($H_2O_2$) for each equivalent of the N-(phosphonomethyl) iminodiacetic acid. And preferably, to obtain the best yields, one employs about 3 moles of the oxidizing agent for each mole of the N-(phosphonomethyl) iminodiacetic acid.

The process of the instant invention is carried out in an aqueous media. It is preferred to employ an aqueous acid media, when a peroxide is employed as the oxidizing agent. Any of the organic or inorganic water-miscible or soluble acids which do not decompose the peroxide and which are not substantially oxidized under the conditions of the reaction can be employed in the process of this invention. The amount of the acid employed is not narrowly critical and can range from as low as 1 part acid per 100 parts of the N-(phosphonomethyl) iminodiacetic acid to 100 parts of acid per 1 part of N-(phosphonomethyl) iminodiacetic acid. As the temperature of the reaction is increased, higher acid concentrations are beneficial.

When a free oxygen-containing gas is employed as the oxidizing agent, it is preferred to employ a saturated solution of N-(phosphonomethyl) iminodiacetic acid in water. However, for ease of operation, the process is also operable at lower or higher concentrations of the N-(phosphonomethyl) iminodiacetic acid in water.

The time of reaction is not narrowly critical and can vary from as low as 1 minute heating time to as high as 40 or more hours. Of course, it is obvious to those skilled in the art that the yield of product will vary with the reaction time and the temperature of the reaction. For example, a short reaction time at low reaction temperatures, that is temperatures lower than about 70°C., would give very low yields of the product. It is preferred to conduct the instant reaction at a temperature of at least 70°C. and for a period of at least 1 hour to insure complete reaction and ease of recovery of the product.

The process of the instant invention can be conducted at atmospheric, sub-atmospheric or super-atmospheric pressure. It is preferred to conduct the instant process at atmospheric or sub-atmospheric pressure for ease of reaction and economics when liquid or solid oxidizing agents are employed. When the gaseous oxidizing agents are employed, super-atmospheric pressures are sometimes advantageous.

The acids that can be employed in the process of this invention to acidify the aqueous medium include both the organic acids and the inorganic acids. The inorganic acids are, for example, sulfuric acid, hydrofluoric, phosphoric, fluorosulfonic, pyrophosphoric, nitric acid and the like. The organic acids which are useful in the present invention include the water-soluble or miscible organic acids and are for example, acetic, propionic, formic, mono-di- and tri-chloro acetic, mono-, di- and trifluoroacetic, benzenesulfonic, p-toluene, sulfonic, benzenephosphonic acid and the like.

The oxidizing agents which can be employed in the process of the instant invention include oxidizing agents such as the inorganic peroxides, including hydrogen peroxide and organic peroxides. The organic peroxide oxidizing agents include performic acid, peracetic acid, perbenzoic acid, peroxy trifluoroacetic acid, m-chloroperbenzoic, benzoyl peroxide, benzene persulfonic acid and the like. Other inorganic oxidizing agents include oxygen, air or other free oxygen-containing gases in the presence of metallic catalysts (Pt, Pd, Rh, Ir, Ru, etc.) or ultraviolet light, permanganic acid, dichromic acid, chlorine dioxide, persulfuric acid, perboric acid and the like.

The N-(phosphonomethyl) iminodiacetic acid starting material can be prepared by methods known in the art. For example, this material can be produced by the reaction of formaldehyde, iminodiacetic acid and orthophosphorous acid in the presence of sulfuric acid. The N-(phosphonomethyl) iminodiacetic acid mixture resulting from this reaction can be employed per se in the process of this invention. It is preferred to isolate the N-(phosphonomethyl) iminodiacetic acid and then employ it in the process of this invention.

The organic solvent which is employed in the isolation of the product of this invention is one of the water-miscible organic solvents and may include alcohols such as methanol, ethanol isopropanol, butanol and the like, dioxane, and other water soluble heterocyclics and the like; ketones such as acetone, methylethyl ketone and the like; glycols and polyglycols, for example ethylene glycol, propylene glycol, diethylene glycol, methyl cellosolve, dimethyl cellosolve, glycerol and the like. Many other water-miscible organic solvents that can be employed in isolating the product of this invention will be apparent to those skilled in the art.

The compounds produced by the process of this invention are useful as herbicides and plant growth regulators.

The following examples serve to further illustrate the invention. All parts are parts by weight unless otherwise expressly set forth.

EXAMPLE 1

A mixture of N-(phosphonomethyl) iminodiacetic acid (13.7 grams, 0.06 mole), water (20 mls) and concentrated sulfuric acid (6.0 g., 0.06 mole) was heated with stirring at 82°–87°C. as 23 milliliters of 30% hydrogen peroxide was added dropwise over a 2 hour period. After the addition was complete, stirring was continued at 85°C. until a colorless solution was obtained. A nuclear magnetic resonance analysis at this point indicated that a substantial amount of N-phosphonomethyl glycine was present with unreacted starting material. Therefore, an additional 5 milliliters of 30% hydrogen peroxide was added over a 1 hour period after which heating was continued for 4 hours at 82°–87°C. On cooling to room temperature, a white crystalline precipitate, identified as N-phosphonomethyl glycine, was formed. The reaction mixture was diluted with excess ethanol and stored overnight at approximately 0°C. in a refrigerator. The precipitated product was collected, washed with ethanol and diethyl ether and air dried. The yield of essentially pure white crystalline N-phosphonomethyl glycine was 7.8 grams. An additional 0.2 grams of the product was obtained on storage of the filtrate in the refrigerator. The purity of the product was determined by infrared and nuclear magnetic resonance spectral analysis.

EXAMPLE 2

Thirty-nine parts of water and 39 parts of concentrated sulfuric acid were charged into a suitable reaction vessel and then 20 parts of N-(phosphonomethyl) iminodiacetic acid added. The mixture was heated to 80°C. and then 277 parts of a 35% hydrogen peroxide solution was added over a period of from 6½ to 7 hours while maintaining the temperature at 77°–81°C. During the addition of the hydrogen peroxide, 8 additional 20 part increments of N-(phosphonomethyl) iminodiacetic acid were added over a 4 hour period. The reaction was then heated at 80°C. with stirring until nuclear magnetic resonance spectral analysis showed that the reaction was essentially complete. The mixture was then cooled at 0°C. overnight, centrifuged, washed with a small amount of water and dried under vacuum to yield approximately 100 parts of N-phosphonomethyl glycine.

EXAMPLE 3

N-Phosphonomethyl iminodiacetic acid (191.9 parts) and water (168.3 parts) are charged into a suitable reactor. The mixture is then stirred and sulfuric acid (98%, 103.2 parts) is added while the temperature rose to 80°–90°C. A vacuum of 6 inches to 8 inches of mercury is placed upon the system and the mixture heated and the vacuum adjusted so as to maintain the temperature at about 98°C. to 102°C. Hydrogen peroxide (35%, 245.5 parts) is then added over a 4 hour period at a constant rate. Distillate (217 parts) is removed during this period at a constant rate. The reaction mixture is maintained at 100°C. for an additional 15 minutes and then cooled so as to cause crystallization of the N-phosphonomethyl glycine which is recovered by filtration.

EXAMPLE 4

A mixture of N-(phosphonomethyl) iminodiacetic acid (2.3 g.), water (20 ml.) and sodium chlorite (0.9 g.) was charged into a glass reactor and stirred at room temperature. The mixture turned yellow and the temperature began to rise. When the temperature reached 35°C., a yellow gas evolved and a cold water bath was employed to maintain the temperature at about 20°C. for several hours, resulting in a colorless mixture. A sample of the water solution was analyzed by nuclear magnetic resonance spectral analysis, which indicated that oxidation had taken place. An additional amount of sodium chlorite (0.9 g.) was added portion wise at room temperature and the reaction mixture allowed to decolorize as before with the incremental additions of the sodium chlorite taking about 2 hours. At the end of this time, the mixture was almost homogenous. The mixture was concentrated at reduced pressure and the residue washed with methanol and diethyl ether to yield a white powder. Nuclear magnetic resonance spectral analysis of the white powder indicated that it was predominantly N-phosphonomethyl glycine.

Other oxidizing agents which can be substituted for sodium chlorite include meta-chloroperoxybenzoic acid, sodium peroxide, sodium perborate, potassium persulfate, dibenzoyl peroxide, peracetic acid, potassium permanganate, potassium ferrocyanide, chlorine dioxide, sodium dichromate and chromic acid and the like.

EXAMPLE 5

This example illustrates the oxidation of N-(phosphonomethyl) iminodiacetic acid employing a free oxygen-containing gas and platinum on charcoal catalyst.

The platinum catalyst was prepared as follows. To a solution of chloroplatinic acid (0.1 gram) in 40 milliliters of water and 1 gram of decolorizing carbon, sodium borohydride, $NaBH_4$, (0.19 gram) was added gradually with stirring. When the vigorous reaction subsided, the mixture was allowed to stand at room temperature for 5 minutes and then concentrated hydrochloric acid was added dropwise until the pH was approximately 3 to 4, this required 0.8 milliliters of concentrated hydrochloric acid. The catalyst mixture was transferred to a tubular reactor, N-(phosphonomethyl) iminodiacetic acid (2.3 grams) was added and nitrogen blown through the mixture while heating to reflux. Air was blown into the mixture at reflux for 26½ hours.

The mixture was then filtered hot and the residue washed with water. The colorless filtrate was concentrated at reduced pressure on a warm water bath. The residue was washed with ethanol, methanol and diethyl ether and then air dried to yield crystals weighing 1.76 grams. These crystals were determined by nuclear magnetic resonance spectral analysis to be essentially pure N-phosphonomethyl glycine.

When oxygen or a free oxygen-containing gas is substituted for air in the above example, similar results are obtained.

EXAMPLE 6

In this example, a palladium on charcoal catalyst was prepared according to the method used in the previous examples to prepare the platinum catalyst, except that palladium chloride was employed as a source of palladium.

After preparation of the catalyst, the catalyst was transferred to a tubular reactor, N-(phosphonomethyl) iminodiacetic acid (2.3 grams) added, and nitrogen blown through this mixture while heating to reflux. The nitrogen stream was replaced by air and air blown through the mixture for 6 hours. At this time, analysis of a sample of the solution indicated that N-phosphonomethyl glycine was present in the mixture. The oxidation was continued for an additional 22 hours at which time nuclear magnetic resonance spectral analysis of the colorless oxidation solution indicated the presence of substantial amounts of N-phosphonomethyl glycine. This N-phosphonomethyl glycine was recovered by concentration of the solution to dryness and recrystallization of the residue from water.

When oxygen or a free oxygen-containing gas is substituted for air in the above example, similar results are obtained.

EXAMPLE 7

Into a glass reaction vessel was charged N-(phosphonomethyl) iminodiacetic acid (14.0 grams), water (250 milliliters) and 0.2 grams of a 5% rhodium on charcoal catalyst. The mixture was heated to 90°C. and oxygen continuously blown through the mixture with stirring at a rate of 100 milliliters of oxygen per minute. Oxygen was blown through this mixture for a total of 17 hours while maintaining the temperature at 90°C. After removal of the catalyst by filtration, nuclear magnetic resonance spectral analysis indicated the solution to contain N-phosphonomethyl glycine as essentially the only ingredient. The N-phosphonomethyl glycine was recovered by evaporation of the solvent and crystallization of the residue.

EXAMPLE 8

When the procedure of the preceding example was employed, but air was substituted for oxygen and the air oxidation continued for 48 hours, it was found that one obtains an 83% yield of N-phosphonomethyl glycine.

When the pH of the solution is adjusted to 8.5 and the procedure of the preceding example employed, for air oxidation for 71 hours, it was found that yields of approximately 16% of N-phosphonomethyl glycine were obtained.

Similar results are obtained employing the procedure of the previous three examples and air or oxygen as the oxidizing agent in the presence of other platinum group catalysts such as iridium, osmium or ruthenium.

EXAMPLE 9

A mixture of 10 g. of N-(phosphonomethyl) iminodiacetic acid, 170 mls. of water and 0.6 g. of commercial 5% palladium on carbon catalyst was placed in a pressure vessel and oxygen admitted to a pressure of 30 pounds per square inch. The mixture was continuously shaken at this pressure for 3 hours while maintaining the temperature at 90°–100°C. After cooling to room temperature, excess oxygen was vented, the catalyst removed by filtration and the filtrate concentrated to dryness at reduced pressure. The yield of 97% pure N-phosphonomethyl glycine was 7.3 g. (96% yield).

When the above described conditions were employed but with 5% rhodium on carbon in place of palladium on carbon as catalyst, there was produced 7.2 g. of 97% pure N-phosphonomethyl glycine.

EXAMPLE 10

A mixture of 28 g. of N-(phosphonomethyl) iminodiacetic acid, 500 mls. of water and 1 g. of commercial 5% rhodium on carbon catalyst was sealed in an autoclave and heated to 80°C. over a 2 hour period. The autoclave was then pressurized to 1040 pounds per square inch with oxygen and heating continued for an additional 75 minutes. After venting, the catalyst was removed by filtration and the filtrate concentrated at reduced pressure. The residue (15 g.) was essentially pure N-phosphonomethyl glycine as indicated by the nuclear magnetic resonance spectrum.

EXAMPLE 11

This method illustrates the use of immiscible organic solvents to control the exothermic reaction and enhance the yield.

To a mixture of 44.5 lbs. of 66° Be sulfuric acid and 40 lbs. of water was added 70 lbs. of 95% N-(phosphonomethyl) iminodiacetic acid, 24 lbs. of perchloroethylene and 18 lbs. of carbon tetrachloride. The mixture was heated to the reflux temperature after which 34 lbs. of 50% hydrogen peroxide was added during 1 hour. The mixture was then cooled and an additional 132 lbs. of 95% N-(phosphonomethyl) iminodiacetic acid added. The temperature was finally maintained at 85°C. as 186 lbs. of 50% hydrogen peroxide was added during eight hours and 14 lbs. of 50% hydrogen peroxide was added in a final 1 hour period. Heating at 85°C. was continued for 15 minutes after which vacuum was applied and solvents distilled from the reaction mixture at 78°–17.5°C. The residual mixture was cooled to 0°C., stirred at this temperature for 5 hours and then filtered. The filter cake was washed with 25 lbs. of water and dried to yield 105 lbs. of 95% pure N-phosphonomethyl glycine.

In conducting the process of the instant invention, it is desirable to have intimate contact of the oxidizing agent with the N-(phosphonomethyl) iminodiacetic acid reactant. Such contact can be attained by methods known to those in the art. For example, where the reagents are solids or are soluble in water, the mixture can be stirred or shaken to insure such contact. Where a gaseous oxidizing agent is employed, such contact can be obtained by dispersing the free oxygen-containing gas through a diffuser such as a porous glass frit or by stirring, shaking or other methods known to those skilled in the art. When a gaseous oxidizing agent is employed, it is sometimes advantageous to conduct the reaction at pressures above atmospheric with stirring or shaking to insure better contact of the oxidizing agent with the N-(phosphonomethyl) iminodiacetic acid.

What is claimed is:

1. A process for the production of N-phosphonomethyl glycine which comprises forming an admixture of N-(phosphonomethyl)iminodiacetic acid, water and a metallic catalyst selected from the class consisting of platinum, palladium, rhodium, iridium, ruthenium or osmium, heating said admixture to an elevated temperature and contacting said admixture with a free oxygen-containing gas whereby said N-(phosphonomethyl)iminodiacetic acid is oxidized to yield N-phosphonomethyl glycine.

2. The process of claim 1 wherein the free oxygen-containing gas is air.

3. The process of claim 1 wherein the free oxygen-containing gas is oxygen.

4. The process of claim 2 wherein the catalyst is rhodium.

5. The process of claim 2 wherein the catalyst is platinum.

6. The process of claim 2 wherein the catalyst is palladium.

7. The process of claim 3 wherein the catalyst is rhodium.

8. The process of claim 3 wherein the catalyst is platinum.

9. The process of claim 3 wherein the catalyst is palladium.

10. The process of claim 1 wherein the reaction is conducted at super atmospheric pressure and the temperature is from 90°C. to about 120°C.

11. The process of claim 10 wherein the catalyst is platinum.

12. The process of claim 10 wherein the catalyst is palladium.

13. The process of claim 10 wherein the catalyst is rhodium.

* * * * *